United States Patent [19]

Meilland, deceased

[11] Patent Number: Plant 6,803

[45] Date of Patent: May 16, 1989

[54] ROSE PLANT—MEICLADOR VARIETY

[75] Inventor: Marie-Louise Meilland, deceased, late of Antibes, France, by Jean-Pierre Le Naour, legal representative

[73] Assignee: The Conard-Pyle Company, West Grove, Pa.

[21] Appl. No.: 136,381

[22] Filed: Dec. 22, 1987

[51] Int. Cl.[4] ..... A01H 5/00

[52] U.S. Cl. ..... Plt./15

[58] Field of Search ..... Plt./15

*Primary Examiner*—Robert E. Bagwill

*Attorney, Agent, or Firm*—Burns, Doane, Swecker & Mathis

[57] ABSTRACT

A new and distinct variety of Hybrid Tea rose plant is provided which forms abundantly and continuously elegant double intensely golden yellow blossoms which possess a long vase life. The plant exhibits vigorous vegetation and is well suited for forcing and cut flower production. Such blooming continues well during the winter under greenhouse conditions. The plant is not particularly affected by cryptogamic diseases.

1 Drawing Sheet

SUMMARY OF THE INVENTION

The new variety of Hybrid Tea rose plant was created by artificial pollination wherein two parents were crossed which previously had been studied in the hope that they would contribute the desired characteristics. The female parent (i.e., the seed parent) of the new variety was the product of the pollination of the Sweet Promise variety (U.S. Plant Pat. No. 3,095) by the Meilimona variety (U.S. Plant Pat. No. 4,013). The Sweet Promise variety sometimes is called the Sonia variety. The Meilimona variety sometimes is called the Banzai variety. The male parent (i.e., the pollen parent) was the Meirobidor variety (U.S. Plant Pat. No. 5,042). The parentage of the new variety can be summarized as follows:

[Sweet Promise×Meilimona]×Meirobidor.

The seeds resulting from the above pollination were sown in a greenhouse and 586 plantlets were obtained which were physically and biologically different from each other. Selective study resulted in the identification of a single plant of the new variety.

It was found that the new variety of Hybrid Tea rose plant of the present invention possesses the following combination of characteristics:

(a) forms in abundance elegant double golden yellow blossoms,
(b) is well adapted for forcing,
(c) exhibits vigorous vegetation, and
(d) is particularly suited for cut flower production.

The new variety well meets the needs of the cut flower industry since the plant blossoms continuously and abundantly especially during the winter. It also is suited for other horticultural uses.

The new variety has been found to undergo asexual propagation by a number of routes, including budding, grafting, cuttage, etc. The characteristics of the new variety have been found to be strictly transmissible by such asexual propagation from one generation to another.

The new variety has been named the Meiclador variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were two years of age and were observed during January while grafted on *Rosa indicia* and growing in a greenhouse at Cap d'Antibes, France.

FIG. 13 illustrates a specimen of a main branch;

DETAILED DESCRIPTION

Figures 1, 2, 3, 4, 5, 6, 7, 8, 9, 10, 11, 12, 14, 15, 16:
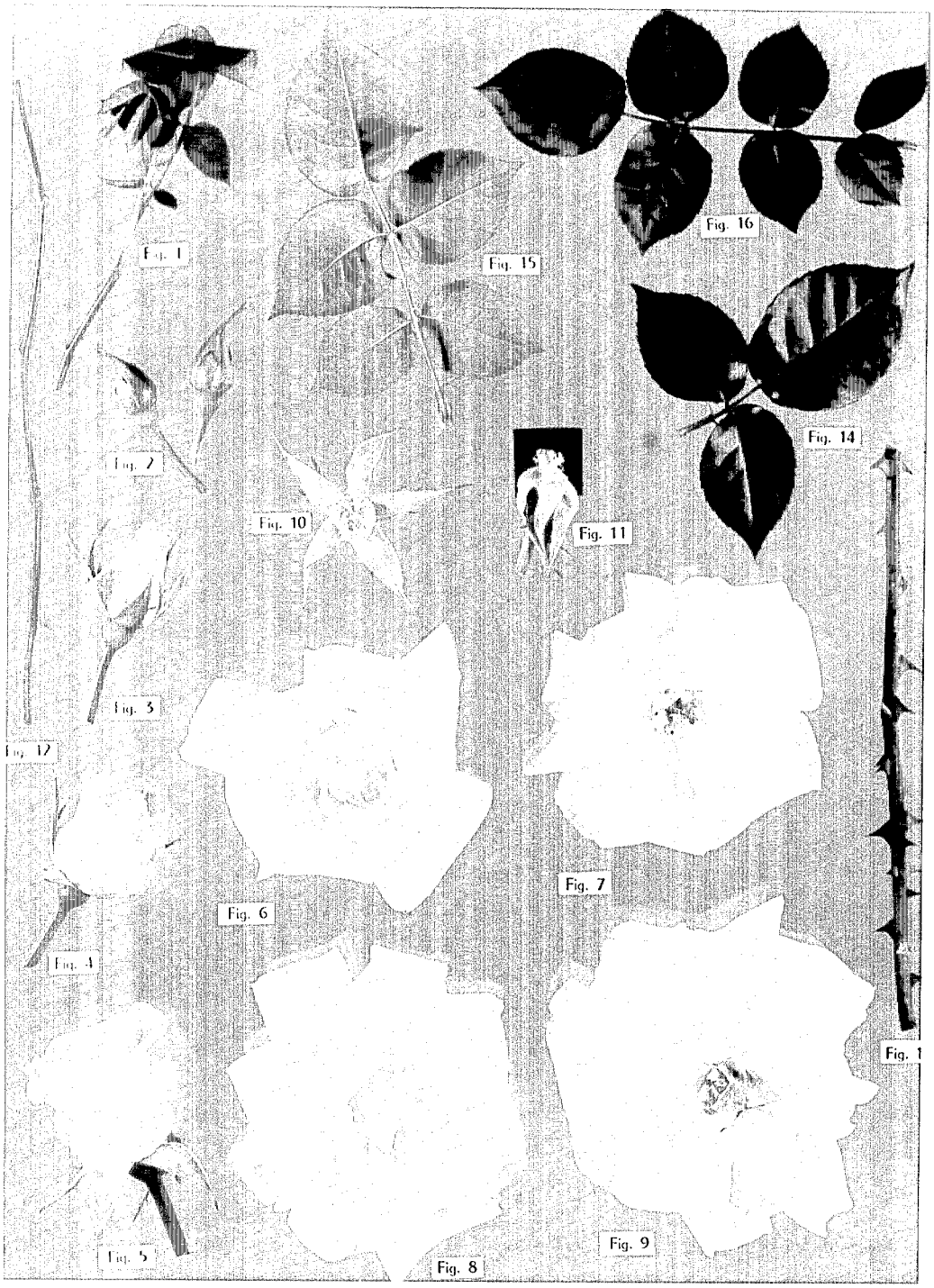
FIG. 1 illustrates a specimen of a young shoot.
FIG. 2 illustrates a specimen of two floral buds before the opening of the sepals.
FIG. 3 illustrates a specimen of a floral bud at the opening of the sepals.
FIG. 4 illustrates a specimen of a floral bud at the opening of the petals.
FIG. 5 illustrates a specimen of a flower in the course of opening.
FIG. 6 illustrates a specimen of a fully open flower—plan view—obverse.
FIG. 7 illustrates a specimen of a fully open flower—plan view—reverse.
FIG. 8 illustrates a specimen of a fully open flower immediately prior to petal drop—plan view—obverse.
FIG. 9 illustrates a specimen of a fully open flower immediately prior to petal drop—plan view—reverse.
FIG. 10 illustrates a specimen of a floral receptacle showing the arrangement of the stamens and pistils.
FIG. 11 illustrates a specimen of a floral receptacle showing the arrangement of the pistils (stamens removed)
FIG. 12 illustrates a specimen of a flowering stem.
FIG. 14 illustrates a specimen of a leaf with three leaflets—plan view—upper surface.
FIG. 15 illustrates a specimen of a leaf with five leaflets—plan view—under surface.
FIG. 16 illustrates a specimen of a leaf with seven leaflets—plan view—upper surface.

The chart used in the identification of the colors is that of The Royal Horticultural Society (R.H.S. Colour Chart). The description is based on two year old plants made during January while grafted on *Rosa indicia* understock and growing in a greenhouse at Cap d'Antibes, France. The coloration in common terms precedes reference to the chart.

Class: Hybrid Tea.

Plant:

*Height.*—Plants where were pruned to a height of 85 cm. produce floral stems having a length of approximately 40 to 70 cm.

*Habit.*—Erect.

Branches:

*Color.*—Young stems: light green, Green Group 137C, more or less shaded with reddish brown. Adult wood: medium green, Yellow-Green Group 146A.

Leaves:

*Stipules.13* Adnate, pectinate, wide and linear.

*Petioles.*—Upper surface: grooved, reddish brown on young leaves and medium green on adult foliage with more or less glandular edges. Under surface: medium green, smooth, bear some thorns.

*Leaflets.*—Number: 3, 5 (most often), and 7. Shape: oval. Serration: simple and regular. Texture: firm. General appearance: ample foliage with a glossy aspect. Color (young foliage): upper surface: reddish brown. under surface: reddish brown. Color (adult foliage): upper surface: dark green, Yellow-Green Group 147A. under surface: light green, Green Group 137C.

Inflorescence:

*Number of flowers.*—Generally one per stem.

*Peduncle.*—Straight, rigid, medium green in coloration, and smooth. The length is approximately 9.5 to 10.5 cm. on average.

*Sepals.*—Upper surface: tomentose, greenish in coloration. Under surface: smooth, light green in coloration, the edges are slightly appendiculated.

*Buds.*—Shape: oblong. Length: approximately 4.5 cm. on average. Size: large. Color upon opening: Upper surface: golden yellow, Yellow Group 12A. Under surface: golden yellow, Yellow Group 12A.

*Flower.*—Shape: initially long with a high center changing to the configuration of a deep cup. Diameter: approximately 10 to 11 cm. on average. Color (when opening begins): upper surface: golden yellow, Yellow Group 12A and lightening to Yellow Group 12C on the outside petals. under surface: same as upper surface. Color (when blooming): upper surface: golden yellow, Yellow Group 12A and lightening to Yellow Group 12C on the outside petals. under surface: same as upper surface. Color (at end of opening): upper surface: golden yellow, Yellow Group 12A and lightening to Yellow Group 12C on the outside petals. under surface: same as upper surface. Fragrance: average and spicy. Lasting quality: long. Petal number: approximately 35 to 38 on average. Petal form: generally rounded with reflected edges. Texture: firm. petal drop: very good. stamen number: approximately 212 to 216 on average. anthers: normal, light yellow in coloration, located beyond the stigmas with inserted ends. filaments: normal, golden yellow in coloration, of irregular heights. pistils: approximately 133 to 136 on average. stigmas: normal, straw colored, often two are joined. styles: straw colored, with light fuchsine tips, of irregular heights. receptacle: light green, smooth at the dehiscence of the anthers, in longitudinal section are wide and in the shape of a jug.

Development:

*Vegetation.*—Vigorous.

*Blooming.*—Abundant and continuous.

*Resistance to diseases.*—Good.

*Aptitude to forcing.*—Excellent.

It is claimed:

1. A new and distinct variety of Hybrid Tea rose plant characterized by the following combination of characteristics:

(a) forms in abundance elegant double golden yellow blossoms, (b) is well adapted for forcing, (c) exhibits vigorous vegetation, and (d) is particularly suited for cut flower production;

substantially as herein shown and described, together with the parts thereof.

* * * * *